United States Patent [19]

Hanifl et al.

[11] Patent Number: 5,299,687
[45] Date of Patent: Apr. 5, 1994

[54] CANNULA ADAPTOR DELIVERY SYSTEM

[75] Inventors: Paul H. Hanifl, Barrington Hills; Lawrence G. Ponsi, Wheeling; David A. Bates, Libertyville, all of Ill.

[73] Assignee: Sage Products, Inc., Crystal Lake, Ill.

[21] Appl. No.: 995,152

[22] Filed: Dec. 22, 1992

[51] Int. Cl.5 .......................................... B65D 83/10
[52] U.S. Cl. .................... 206/370; 206/364; 206/366; 206/460
[58] Field of Search ............... 206/364, 366, 370, 378, 206/460, 503; 128/763; 604/240

[56] References Cited

U.S. PATENT DOCUMENTS

| | | | |
|---|---|---|---|
| 2,435,994 | 2/1948 | Zukerman | 206/366 |
| 3,391,814 | 7/1968 | Box | 206/503 |
| 4,046,254 | 9/1977 | Kramer | 206/370 |
| 4,154,795 | 5/1979 | Thorne | 206/460 |
| 4,182,448 | 1/1980 | Hack et al. | 206/460 |
| 4,420,085 | 12/1983 | Wilson et al. | 206/370 |
| 4,421,230 | 12/1983 | Stanton | 206/378 |
| 4,596,562 | 6/1986 | Vernon | 206/370 |
| 4,688,672 | 8/1987 | Pemberton | 206/378 |
| 4,941,571 | 7/1990 | Barrett et al. | 206/378 |
| 5,025,923 | 6/1991 | Okui | 206/460 |
| 5,099,992 | 3/1992 | Heimreid | 206/370 |
| 5,117,837 | 6/1992 | Wanamaker et al. | 128/763 |

Primary Examiner—David T. Fidei
Attorney, Agent, or Firm—Lee, Mann, Smith, McWilliams, Sweeney & Ohlson

[57] ABSTRACT

A system for holding and delivery a plurality of disposable cannula adaptors. A dispenser is provided with a dispensing surface having a series of posts or other means for retaining a plurality of disposable cannula adaptors in a spaced relationship. The posts extend upwardly, and preferably two or more adaptors can be accommodated on each post. A plurality of the dispensers can be employed in a stacked relationship, with the dispensers having the posts extending from one side thereof and one or more post retainers formed on the opposite side and in alignment with a post on the next lower dispenser. In an alternative form, the dispenser has an adhesive dispensing surface, and the cannula adaptors are applied in a spaced relationship to the adhesive surface.

14 Claims, 2 Drawing Sheets

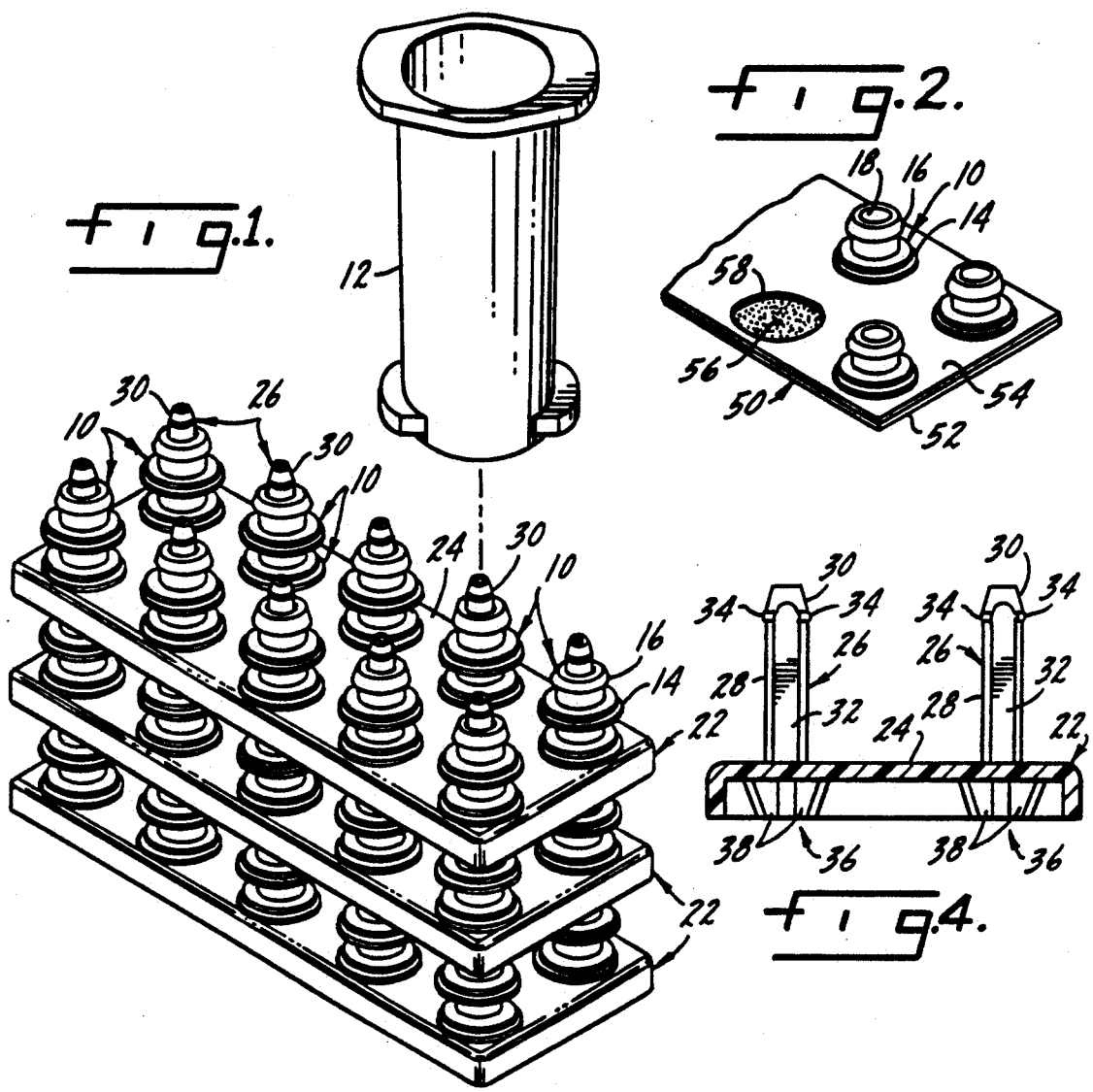
Fig. 1.
Fig. 2.
Fig. 4.
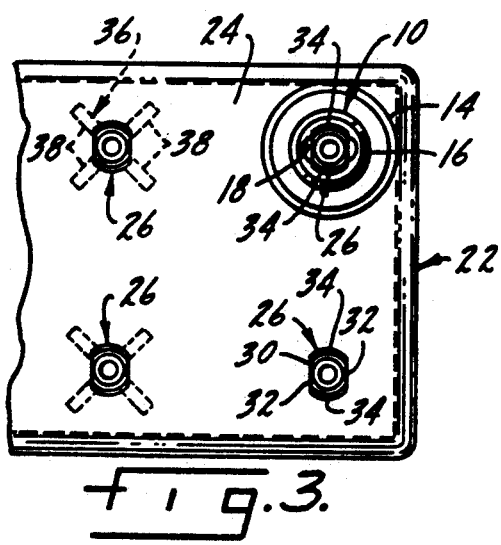
Fig. 3.
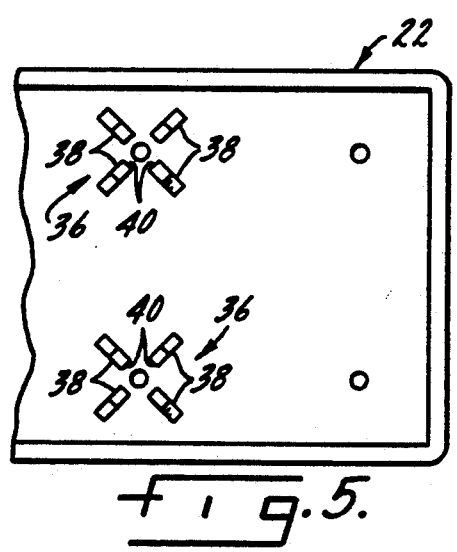
Fig. 5.

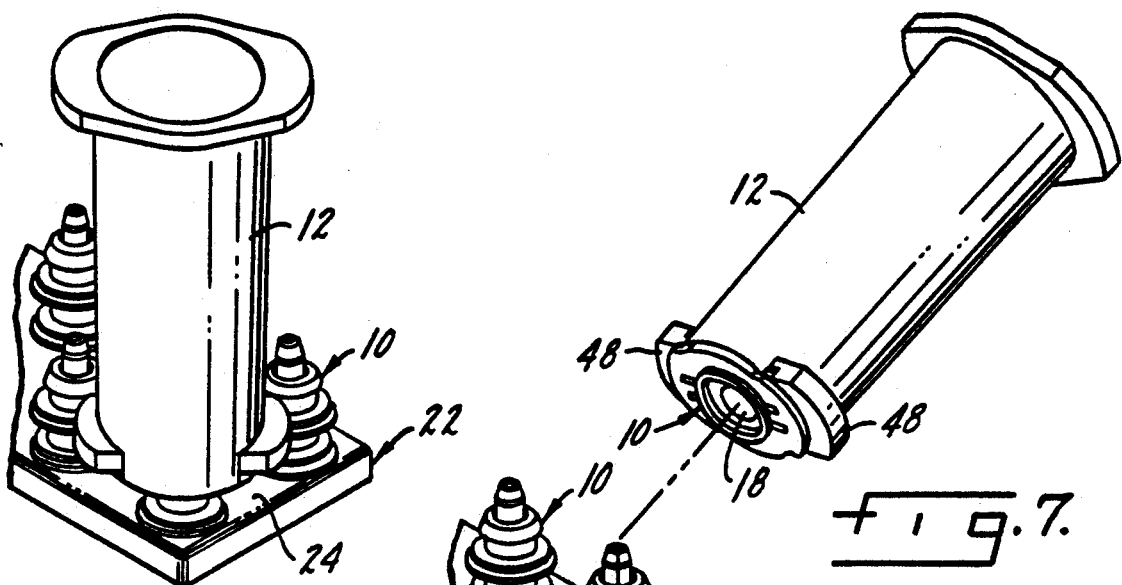
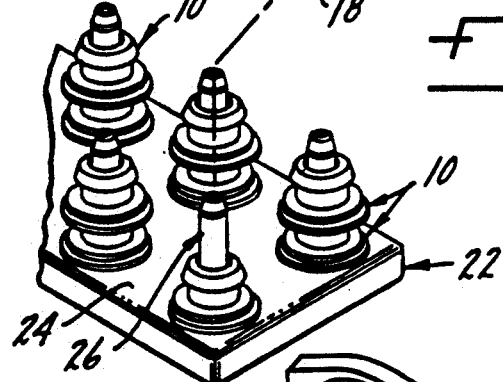
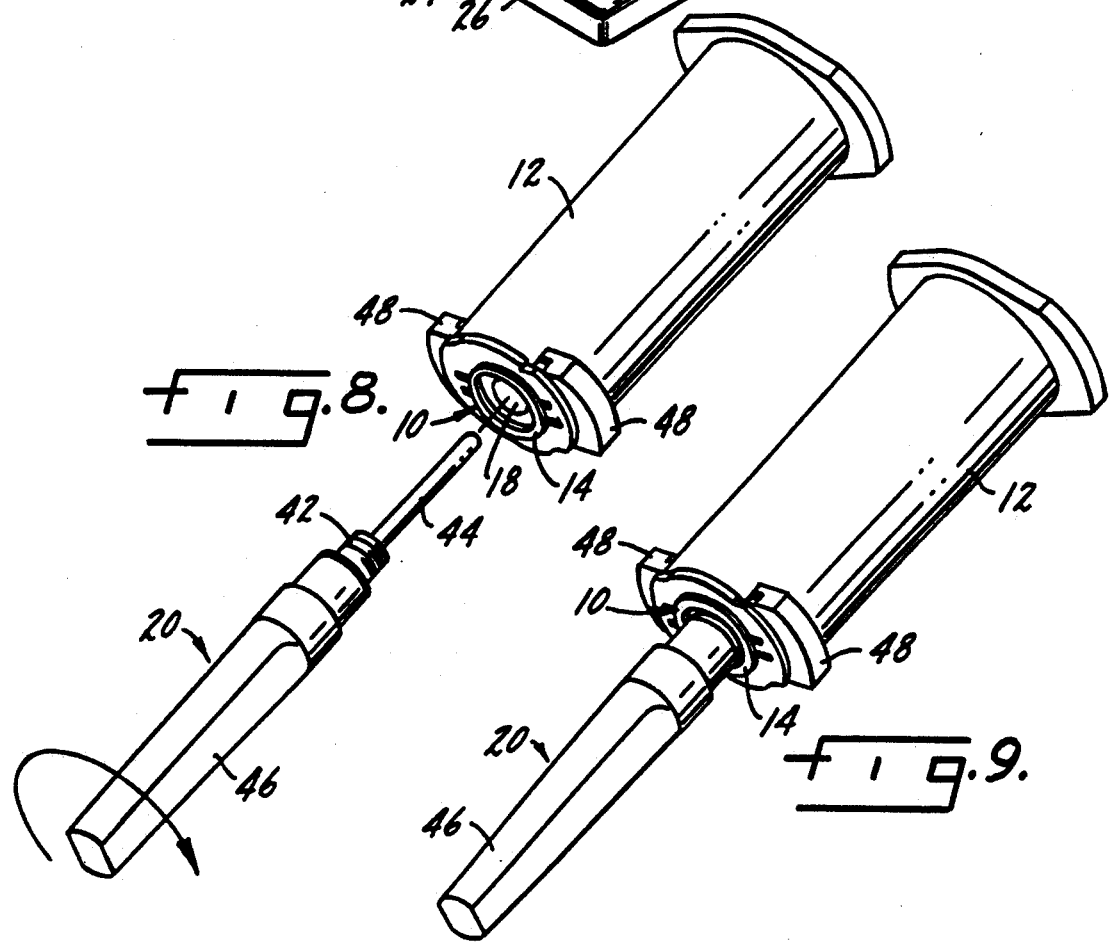

CANNULA ADAPTOR DELIVERY SYSTEM

BACKGROUND OF THE INVENTION

This invention relates to blood sampling apparatus, and more particularly to a system for delivering a plurality of disposable cannula adaptors, each of which is formed to be retained in a holder for engagement of a cannula.

As medical science has advanced, the sampling and analysis of a patient's blood has become an important diagnostic aid. However, blood collection can also pose hazards for the person drawing blood, and therefore various devices have been developed to protect the drawer from contamination as much as possible.

U.S. Pat. Nos. 4,841,985; 4,984,580 and 5,117,837 are directed to various developments in blood drawing apparatus, and the disclosures of said patents are incorporated herein by reference. In one form of the blood drawing apparatus of such patents, a disposable cannula adaptor is employed in connection with a holder for an evacuated blood collection tube. The cannula adaptor is inserted in one end of the holder and held temporarily in place, and a blood needle is then screwed into the adaptor, with one end extending outwardly for vein puncture, and an opposite end extending inwardly in the holder for piercing a blood collection tube. After use of the holder to collect blood, the cannula adaptor and cannula are released from the holder, and disposed. The holder can be disposed, or cleaned and reused with a new cannula adaptor.

While the cannula adaptor concept of the incorporated patents provides a significant advance in blood drawing apparatus, proper delivery of the cannula adaptors, to prevent contamination and to provide easy access, remains beyond the scope of the patents.

SUMMARY OF THE INVENTION

The present invention relates to a system for holding and delivering a plurality of disposable cannula adaptors. The system comprises a dispenser having a dispensing surface, and means on the dispensing surface for removably retaining a plurality of disposable cannula adaptors in a spaced relationship.

In accordance with one form of the invention, the retaining means comprises a series of spaced posts, extending from and perpendicular to the dispensing surface. Each post comprises a shaft having one end secured to the dispensing surface and an opposite end shaped to accommodate a cannula adaptor passing over the opposite end.

It is preferred that each shaft includes means proximate the opposite end for temporarily retaining a cannula adaptor on the shaft. That means for temporarily retaining comprises a protrusion extending laterally from the shaft. Each post is of a length sufficient to accommodate at least two cannula adaptors stacked axially on the post.

In the preferred form on the invention, at least two dispensers are employed, with means for joining the dispensers together as a unit. The joining means comprises a plurality of spaced posts, which can also serve as posts for the cannula adaptors, extending from the dispensing surface of one of the dispensers and a plurality of post retainers located in an underside of a second of the dispensers, with the post retainers being located in registration with the posts. Each post retainer comprises a plurality of spaced clamp elements which are shaped to engage a post. Preferably, the dispensers are identical, with each dispenser including a plurality of upstanding posts and a plurality of post retainers on an underside opposite the posts.

In a second form of the invention, the retaining means comprises an adhesive surface on the dispensing surface. In one version of the second form of the invention, a mask overlies the adhesive surface, the mask having a series of spaced apertures therein exposing the adhesive surface for retention of a cannula adaptor on the adhesive surface at each aperture. In a second version, the adhesive comprises a series of spaced adhesive areas on the dispensing surface.

BRIEF DESCRIPTION OF THE DRAWINGS

The invention is described in greater detail in the following description of examples embodying the best mode of the invention, taken in conjunction with the drawing figures, in which:

FIG. 1 is a perspective view of a series of stacked dispensers according to the invention, with a blood needle holder poised above the top dispenser for engaging a disposable cannula adaptor, FIG. 2 is a perspective view of an alternative form of the invention, without a blood needle holder being illustrated, FIG. 3 is an enlarged partial top plan view of one of the dispensers illustrated in FIG. 1, with most of the cannula adaptors omitted except for those on one of the upstanding posts, FIG. 4 is an enlarged cross sectional view of one end of one of the dispensers of FIG. 1, showing post retainers located beneath the dispenser, FIG. 5 is a view similar to FIG. 3, but showing the underside of one of the dispensers, FIG. 6 is a perspective view of a blood needle holder being engaged on one of the posts of the dispenser to capture a disposable cannula adaptor, FIG. 7 is a view similar to FIG. 6, but with the blood needle holder having been withdrawn from the dispenser with a captured cannula adaptor, FIG. 8 illustrates the blood needle holder of FIGS. 6 and 7 after being withdrawn with one of the cannula adaptors therein, and illustrating how a blood needle is inserted in the adaptor, and FIG. 9 illustrates the blood needle holder with the blood needle having been installed therein, but with the sheath for the blood needle remaining in place.

DESCRIPTION OF EXAMPLES EMBODYING THE BEST MODE OF THE INVENTION

FIGS. 1 and 3–7 illustrate one form of the invention for delivering a plurality of disposable cannula adaptors, shown generally at 10 in the drawing figures. The cannula adaptors 10 are shaped to engage a blood needle holder 12 in the manner illustrated and described in detail in incorporated U.S. Pat. No. 5,117,837, from which description in greater detail can be obtained. Each of the adaptors 10 includes, on its exterior, a crown 14 and a tapered edge 16 which are shaped to appropriately engage the blood needle holder 12. Internally, each adaptor 10 has internal threads 18 (FIG. 3) which are shaped to be engaged on a double ended blood needle or cannula 20 (FIGS. 8 and 9), discussed in greater detail below and in the incorporated references.

In the first form of the invention, the cannula adaptors 10 are located on a series of dispensers 22. Each of the dispensers 22 includes a top dispensing surface 24 with means for removably retaining a plurality of the disposable cannula adaptors in a spaced relationship, in this form comprising a series of upstanding, spaced posts 26 which extend from and are perpendicular to the dispensing surface 24.

Each of the posts 26, as best shown in FIGS. 3 and 4, is composed of an elongated shaft 28 having one end secured to the dispensing surface 24 and an opposite end having a taper 30 which is shaped to accommodate a cannula adaptor 10 passing thereover. Opposite sides 32 of the shaft 28 are flat, although the shaft 28 may be entirely cylindrical, if desired.

The shafts 28 are sized so that the internal threads 18 of the cannula adaptors 10 pass easily thereover. To retain the adaptors 10 on the shafts 28 until removal is desired, each of the shafts 28 includes at least one small protrusion extending laterally from the shaft at the bottom of the taper 30. While a pair of protrusions 34 are shown in the drawing figures on opposite sides of each of the shafts 28, a single protrusion 34 may be adequate.

Preferably, the dispensers 22 are molded of a suitable plastic material, with the posts 26 being of the same material. The protrusions 34 extend laterally outwardly sufficiently to engage the threads 18 so that an adaptor 10 can be "snapped" over a post 26. Alternatively, since the internal threads 18 are helical, an adaptor can be engaged on a protrusion 34 and rotated to be screwed onto a post 26 or removed therefrom.

As shown in FIG. 1, the dispensers 22 are preferably formed to be joined in a vertical stack. For joining the dispensers, not only does each of the dispensers include a series of the spaced posts 26, but also each of the dispensers includes a series of post retainers 36 on the underside of each of the dispensers 22. Preferably, four of the post retainers 36 are employed, being located in registration with the upstanding posts 26 of the dispenser 22 immediately beneath. Alternatively, a post retainer 36 can be formed in the underside of each dispenser 22 beneath each of the posts 26 in order to engage each of the posts 26 of the next succeeding dispenser, although so many retainers 36 are normally not needed. However, at least one post retainer 36 is required to join two dispensers 22.

Each of the post retainers 36 is composed of four spaced clamp elements 38 which are spaced and shaped to engage a post 26. Because the dispenser 22 is preferably formed of plastic, a frictional engagement with the posts 26 is sufficient, and therefore each of the clamp elements 38 includes a substantially vertical inner surface 40. However, the inner surfaces 40 can be notched or otherwise formed to better engage with the protrusions 34, if additional holding force is required.

As shown in FIG. 1, three of the dispensers 22 are stacked and secured to one another with the posts 26 of one dispenser 22 engaging the post retainers 36 in the underside of the next higher dispenser 22. Any number of dispensers 22 can be stacked as desired. Also, each of the dispensers 22 is shown with a total of ten posts 26 thereon, with two cannula adaptors 10 on each post. Obviously, any number of posts 26 can be formed depending on the sizes of the dispensers 22, and one, two or more of the adaptors 10 can be mounted on a post 26, depending on the height of the post.

FIGS. 1 and 6–9 illustrate the sequence of installing an adaptor 10 in a blood needle holder 12, and subsequent installation of a blood needle 20 in the holder 12. First, the holder 12 is poised above a selected one of the adaptors 10. The holder 12 is then pushed downwardly on to the selected adaptor 10, until the adaptor 10 clicks in place, as shown in FIG. 6. Thereafter, the holder 12 and captured adaptor 10 are lifted vertically upwardly, to remove the adaptor 10 from its post 26. Then, the blood needle 20 is installed by removing a protective sheath (not illustrated), exposing a threaded hub 42 and a protected vessel-puncturing needle 44. The blood needle 20 is then installed in the holder 12 by engaging the threads 42 in the threads 18, until the blood needle 20 is fully engaged, as shown in FIG. 9. A sheath 46 of the blood needle 20 is then removed, exposing the blood drawing needle (not illustrated) for vein puncture.

After blood has been drawn, the blood needle 20 is ejected from the holder 12 by depressing the opposite spring-loaded side locks 48, releasing the adaptor 10 and blood needle so that the holder 12 can be reused or separately discarded. Alternatively, to avoid any risk of contamination, a separate apparatus can be provided to engage the side locks 48, so that the blood needle 20 is ejected without human intervention and thus avoiding the possibility of a needle stick.

An alternative form of the invention is shown in FIG. 2. The adaptors 10 used in this form of the invention are identical, and only the dispenser differs. In this form of the invention, a dispenser 50 is provided, comprising a lower dispensing surface or portion 52, and a mask 54. An adhesive surface 56 is applied to the dispensing portion 52 in order to secure the mask to the dispensing portion.

The mask 54 is provided with a series of spaced apertures 58, exposing the adhesive 56. At each aperture, one of the adaptors 10 is applied, with its crown 14 adhering to the adhesive 56. Thus, the adaptors 10 are spaced periodically due to the spacing of the apertures 58 in the dispenser 50.

Obviously, the adaptors 10 cannot be stacked one atop another on the dispenser 50 as on the dispenser 22. However, the adaptors 10 are removed from the dispenser 50 in the same manner, using a blood needle holder 12 to engage the adaptors 10 and remove them one-at-a-time.

Although the dispenser 50 is shown as a pair of elements with the adhesive 56 therebetween, instead of utilizing a pair of elements, the adhesive 56 can be applied in spots to the top surface of the dispenser 50, performing the same function as the adhesive 56 exposed by the apertures 58 in the mask 54.

Various changes can be made to the invention without departing from the spirit thereof or scope of the following claims.

What is claimed is:

1. A system for holding and delivering a plurality of disposable cannula adaptors, comprising
   a. a dispenser having a dispensing surface,
   b. at least one disposable cannula adaptor, said adaptor having an internal aperture therethrough, and
   c. means on said dispensing surface for removably retaining a plurality of said disposable cannula adaptors in a spaced relationship, said retaining means comprising a series of spaced posts extending from and perpendicular to said dispensing surface, each post comprising a shaft having one end secured to said dispensing surface and an opposite end shaped to pass through said internal aperture when said adaptor is passed said opposite end, and each post having a length sufficient to accommodate at least two cannula adaptors stacked axially on said post.

2. A system according to claim 1 in which each shaft includes means proximate said opposite end for temporarily retaining a cannula adaptor on said shaft.

3. A system according to claim 2 in which said means for temporarily retaining comprises a protrusion extending laterally from said shaft.

4. A system according to claim 1 in which said shaft has opposite flat sides.

5. A system for holding and delivering a plurality of disposable cannula adaptors, comprising
   a. a dispenser having a dispensing surface,
   b. at least one disposable cannula adaptor, said adaptor having a circular crown at one end, and
   c. means on said dispensing surface for removably retaining a plurality of said disposable cannula adaptors in a spaced relationship, said retaining means comprising an adhesive surface on said dispensing surface, said crown adhering to said surface.

6. A system according to claim 5 including a mask overlying said adhesive surface, said mask having a series of spaced apertures therein exposing said adhesive surface for retention of a said cannula adaptor on said adhesive surface at each aperture.

7. A system according to claim 5 in which said adhesive surface comprises a series of spaced adhesive areas on said dispensing surface.

8. A system according to claim 1 including at least two dispensers, and including means for joining said dispensers.

9. A system according to claim 8 in which said joining means comprises a plurality of said spaced posts extending from the dispensing surface of one of said dispensers and a plurality of post retainers located in an underside of a second of said dispensers, said post retainers being located in registration with said posts.

10. A system according to claim 9 in which each post retainer comprises a plurality of spaced clamp elements shaped to engage a post.

11. A system according to claim 9 in which each shaft includes means proximate said opposite end for temporarily retaining a cannula adaptor on said shaft.

12. A system according to claim 11 in which said means for temporarily retaining comprises a protrusion extending laterally from said shaft.

13. A system according to claim 12 in which said protrusion is shaped to engage a said post retainer.

14. A system according to claim 6 in which each aperture is shaped to correspond to said crown.

* * * * *